United States Patent
Tanaka et al.

(10) Patent No.: US 10,080,640 B2
(45) Date of Patent: Sep. 25, 2018

(54) STENT TO BE PLACED IN BILE DUCT

(71) Applicants: NATIONAL UNIVERSITY CORPORATION YAMAGATA UNIVERSITY, Yamagata-shi (JP); PIOLAX MEDICAL DEVICES, INC., Yokohama-shi (JP)

(72) Inventors: Masaru Tanaka, Yonezawa (JP); Makiko Aoki, Yonezawa (JP); Chikako Sato, Yonezawa (JP); Yoshihide Toyokawa, Yokohama (JP); Kyosuke Shirakawa, Yokohama (JP)

(73) Assignees: NATIONAL UNIVERSITY CORPORATION YAMAGATA UNIVERSITY, Yamagata-shi, Yamagata (JP); PIOLAX MEDICAL DEVICES, INC., Yokohama-shi, Kanagawa (JP)

( * ) Notice: Subject to any disclaimer, the term of this patent is extended or adjusted under 35 U.S.C. 154(b) by 78 days.

(21) Appl. No.: 14/785,302

(22) PCT Filed: Apr. 15, 2014

(86) PCT No.: PCT/JP2014/060703
§ 371 (c)(1),
(2) Date: Oct. 16, 2015

(87) PCT Pub. No.: WO2014/171448
PCT Pub. Date: Oct. 23, 2014

(65) Prior Publication Data
US 2016/0074149 A1     Mar. 17, 2016

(30) Foreign Application Priority Data
Apr. 18, 2013  (JP) .................. 2013-087836

(51) Int. Cl.
*A61F 2/07* (2013.01)
*A61F 2/04* (2013.01)
(Continued)

(52) U.S. Cl.
CPC .............. *A61F 2/04* (2013.01); *A61F 2/07* (2013.01); *A61F 2/915* (2013.01); *A61L 31/10* (2013.01);
(Continued)

(58) Field of Classification Search
CPC .......... A61F 2002/041; A61F 2002/072; A61F 2210/0076; A61F 2220/0008;
(Continued)

(56) References Cited

U.S. PATENT DOCUMENTS 4,300,244 A * 11/1981 Bokros ................. A61B 17/11
623/1.13
2002/0000403 A1 * 1/2002 Tanaka ................ A61M 1/3633
210/263
(Continued)

FOREIGN PATENT DOCUMENTS

EP   1 950 567 A1   7/2008
EP   2 656 864 A1   10/2013
(Continued)

OTHER PUBLICATIONS

Inoue et al, Indwelling Tube for Insertion into Vessel, (Jun. 2004), Derwent abstract summary of Ionue et al patent JP-2004174204A.*
(Continued)

*Primary Examiner* — Paul Prebilic
(74) *Attorney, Agent, or Firm* — McGinn I.P. Law Group, PLLC.

(57) ABSTRACT

Provided are a stent to be placed in the bile duct and a process for producing the stent, the stent hollow being less apt to be blocked even when the stent is placed in the bile
(Continued)

duct for a long period. The inner peripheral surface of the stent is coated with a resin layer with resistance to sludge formation that includes a polymer obtained by polymerizing 2-methoxyethyl acrylate. This stent is produced by applying a coating fluid that contains 0.1-0.5 mass % polymer obtained by polymerizing 2-methoxyethyl acrylate, to the inner peripheral surface of a stent.

14 Claims, 8 Drawing Sheets

(51) Int. Cl.
  *A61F 2/915* (2013.01)
  *A61L 31/10* (2006.01)
  *A61F 2/848* (2013.01)

(52) U.S. Cl.
  CPC .......... *A61F 2/848* (2013.01); *A61F 2002/041* (2013.01); *A61F 2002/072* (2013.01); *A61F 2002/9155* (2013.01); *A61F 2002/91575* (2013.01)

(58) Field of Classification Search
  CPC ...... A61F 2230/0069; A61F 2250/0026; A61F 2250/0056
  See application file for complete search history.

(56) References Cited

U.S. PATENT DOCUMENTS

| | | | |
|---|---|---|---|
| 2003/0135268 A1* | 7/2003 | Desai | A61F 2/88 623/1.19 |
| 2004/0230285 A1* | 11/2004 | Gifford, III | A61F 2/013 623/1.11 |
| 2005/0197687 A1* | 9/2005 | Molaei | A61F 2/07 623/1.2 |
| 2006/0136048 A1* | 6/2006 | Pacetti | A61L 31/10 623/1.42 |
| 2006/0216326 A1 | 9/2006 | Pacetti | |
| 2008/0051911 A1* | 2/2008 | Rucker | A61F 2/04 623/23.7 |
| 2008/0208325 A1 | 8/2008 | Helmus et al. | |
| 2009/0216319 A1* | 8/2009 | Kennedy, II | A61L 27/34 623/1.42 |
| 2009/0311675 A1 | 12/2009 | Hosokawa | |
| 2010/0266659 A1* | 10/2010 | Pacetti | A61L 31/048 424/423 |
| 2011/0046717 A1* | 2/2011 | Issenmann | A61F 2/91 623/1.16 |
| 2012/0184029 A1* | 7/2012 | Atanasova | A61L 31/048 435/304.1 |
| 2013/0273372 A1 | 10/2013 | Yamamura et al. | |

FOREIGN PATENT DOCUMENTS

| | | | | |
|---|---|---|---|---|
| JP | 8141090 A | * | 6/1996 | |
| JP | 2004174204 A | * | 6/2004 | ............. A61M 1/00 |
| JP | 2004-298223 A | | 10/2004 | |
| JP | 2008-534062 A | | 8/2008 | |
| JP | 2010-502298 A | | 1/2010 | |
| JP | 2011-156083 A | | 8/2011 | |
| WO | WO 2006-102418 A2 | | 9/2006 | |
| WO | WO 2007/046450 A1 | | 4/2007 | |
| WO | WO 2008/001865 A1 | | 1/2008 | |
| WO | WO 2008/027720 A2 | | 3/2008 | |
| WO | WO 2008/106176 A1 | | 9/2008 | |
| WO | 2010-518945 A | | 6/2010 | |
| WO | WO 2011/006507 A2 | | 1/2011 | |
| WO | WO 2012/086569 A1 | | 6/2012 | |
| WO | WO 2012/147675 A1 | | 11/2012 | |

OTHER PUBLICATIONS

English translation of Japanese patent application to Yosuke et al (JP8141090A) published Jun. 4, 1996.*
Extended European Search Report dated Nov. 17, 2016.
International Search Report (ISR) (PCT Form PCT/ISA/210), in PCT/JP2014/060703, dated Jul. 22, 2014.
IPEA-409, in PCT/JP2014/060703, dated Apr. 15, 2014.
IPEA-401, in PCT/JP2014/060703, dated Apr. 15, 2014.
IPEA-416, in PCT/JP2014/060703, dated May 12, 2015.

* cited by examiner

STENT TO BE PLACED IN BILE DUCT

TECHNICAL FIELD

The present invention relates to a stent to be placed in bile duct, which is placed in a bile duct, and a method for producing the same.

BACKGROUND ART

A stent is used for applications, for example, an application in which the stent is placed in a stenosed portion or an occluded portion in a tubular organ, such as a bile duct, a ureter, a trachea, a blood vessel, etc., so as to dilate the tubular organ, thereby making bile, blood, or the like easy to flow therethrough, an application in which the stent is placed in a portion where an aneurysm has occurred, so as to prevent the aneurysm from rupturing, or the like.

As the stent, there are exemplified a metallic stent of a cylindrical metal mesh tube, a covered stent in which the outer periphery of a stent body of a cylindrical metal mesh tube is covered by a cover member, a tube stent of a cylindrical resin tube, and the like.

The covered stent and the tube stent have such an advantage that when placed in the tubular organ, invasion of a body tissue into the inside of the stent is readily suppressed.

For example, Patent Literature 1 discloses a covered stent including a cylindrical stent and a cover member provided in the outer peripheral portion of this stent, which is used upon being placed in a body lumen, wherein when the rigidity in the radial direction of the stent is defined as Rfs, the flexural rigidity in the longitudinal axial direction of the stent is defined as Afs, the rigidity in the radial direction of the covered stent is defined as Rfc, and the flexural rigidity in the longitudinal axial direction of the covered stent is defined as Afc, the covered stent satisfies the relationships of (Rfc/Rfs≤1.5) and (Afc/Afs≤2.0), and the cover member is extended by 1.2 to 3.0 times in a diametrically-expanded state along the circumferential direction of the stent.

However, when the stent is placed in a bile conduct, bile is accumulated on the inner surface of the stent, and this is cured to form sludge, such as biliary sludge, etc., so that the stent lumen is readily occlude. In the case of the covered stent or the tube stent, in particular, the stent lumen is readily occluded, and the frequency of replacement by removal and interchange of the stent, or the like increased, so that the load of a patient is liable to increase.

It has been reported that poly(2-methoxyethyl acrylate) (hereinafter also referred to as "PMEA") is a polymer with low platelet adhesiveness, and PMEA is watched as a biocompatible polymer. Then, PMEA is used upon being coated on the surface of a medical instrument or the like coming into contact with blood.

For example, Patent Literature 2 discloses an implantable device having a coating which includes a polymer selected from the group consisting of poly(2-methoxyethyl acrylate) (PMEA), poly(2-hydroxyethyl acrylate) (PHEA), poly(ethyl acrylate) (PEA), (poly(2-ethylhexyl acrylate) (PEHA), poly(2-phenoxyethyl acrylate) (PPEA), poly(2-ethoxyethyl acrylate) (PEEA), poly(2-hydroxyethyl methacrylate) (PHEMA), poly(2-methoxyethyl methacrylate) (PMEMA), poly(ethyl methacrylate) (PEMA), (poly(2-ethylhexyl methacrylate) (PEHMA), poly(2-phenoxyethyl methacrylate) (PPEMA), poly(2-ethoxyethyl methacrylate) (PEEM), and combinations thereof.

Patent Literature 2 describes in paragraph [0030] that: "A stent having the above-described coating is useful for a variety of medical procedures, including, by way of example, treatment of obstructions caused by tumors in bile ducts, esophagus, trachea/bronchi, and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries."

CITATION LIST

Patent Literature

Patent Literature 1: WO 2008-001865-A
Patent Literature 2: JP-2008-534062-A

SUMMARY OF INVENTION

Technical Problem

In Patent Literature 2, the implantable device, such as a stent, etc., is used upon being coated with PMEA or the like. However, the implantable device of Patent Literature 2 is subjective to a medical device chiefly coming into contact with blood, or a treatment of obstructions caused by tumors in biological passageways, but this patent literature does not describe prevention of occlusion of a stent lumen to be caused due to denaturation of a body fluid on the occasion of placing a stent in a bile duct. In addition, Patent Literature 2 does not disclose any specific constitution on how to coat the implantable device with PMEA.

Thus, an object of the present invention is to provide a stent to be placed in bile duct, in which even when the stent is placed in a bile duct over a long period of time, a stent lumen is hardly occluded due to denaturation of a body fluid, and a method for producing the same.

Solution to Problem

The present inventors made extensive and intensive investigations. As a result, it has been found that denaturation of biological components, such as proteins or bile acid contained in bile, etc., participates in a cause of occlusion of a stent lumen on the occasion of placing a stent in a bile duct. That is, the biological components, such as proteins or bile acid contained in bile, etc., exist while taking a stable hydration structure. However, when the bile comes into contact with the stent, these biological components denature on the stent surface and deposit on the stent surface, and sludge, such as biliary sludge, etc., grows by nucleating this deposit, thereby occluding the stent lumen. Then, it has been found that a film formed by a polymer obtained through polymerization of 2-methoxyethyl acrylate hardly denatures biological components, such as proteins or bile acid contained in bile, etc., and these denatured materials and the like hardly deposit, leading to accomplishment of the present invention.

Specifically, the stent to be placed in bile duct according to the present invention is provided as a stent body of a cylindrical metal mesh tube and a cover member covering the outer periphery and/or inner periphery of the stent body, or as a cylindrical resin tube, wherein the inner peripheral surface of the stent is covered by a sludge-resistant resin layer containing a polymer obtained through polymerization of 2-methoxyethyl acrylate.

In accordance with the present invention, by covering the inner peripheral surface of the stent by a sludge-resistant resin layer containing a polymer obtained through polymerization of 2-methoxyethyl acrylate, it is possible to suppress denaturation of biological components, such as proteins or bile acid contained in bile, etc., thereby preventing deposition of these denatured materials and the like on the stent inner peripheral surface. For this reason, even when the stent is placed in a bile duct over a long period of time, the stent lumen is hardly occluded by sludge, such as biliary sludge, etc., whereby the frequency of replacement of the stent can be reduced.

In the stent to be placed in bile duct according to the present invention, the sludge-resistant resin layer is preferably formed by coating a coating liquid containing 0.1 to 0.5 mass % of the polymer obtained through polymerization of 2-methoxyethyl acrylate on the inner peripheral surface of the stent. In accordance with this embodiment, the stent inner peripheral surface can be covered by a sludge-resistant resin layer that is smoother and has a large contact angle.

In the stent to be placed in bile duct according to the present invention, it is preferred that the cover member includes a polyurethane film covering the stent body and a silicone film covering the stent body and the outer periphery of the polyurethane film; and that the sludge-resistant resin layer is formed on the inner periphery of the polyurethane film of the cover member. In accordance with this embodiment, the sludge-resistant resin layer is formed on the inner periphery of the polyurethane film; and hence, adhesion between the both is favorable, the sludge-resistant resin layer becomes hard to peel off, and excellent durability is revealed. In addition, the outer periphery of the polyurethane film is covered by the silicone film that is strong against hydrolysis, and hence, it is possible to prevent hydrolysis of the polyurethane film. In addition, in the case of a single layer made of a silicone film, pinholes are apt to be produced, so that it is difficult to achieve thinning; however, by covering the silicone film on the outer periphery of the polyurethane member having a high affinity with a silicone resin, it is possible to make the silicone film thin and form it uniformly, so that it becomes possible to downsize the stent. According to this, it is possible to receive the stent even in a catheter with a small inner diameter, and in the case of placing the stent between the stomach and the bile duct or between the duodenum and the bile duct through an ultrasonic endoscope, it becomes possible to decrease the number of times of use of a tube, a dilator, or the like for enlarging a catheter insertion hole, thereby making a hole formed in the bile duct or the like small and enabling invasion into the body to be suppressed. Furthermore, in the case where a hole is formed in the bile duct, it is possible to decrease the quantity of bile leaking out from the bile duct into the abdominal cavity, thereby suppressing peritonitis.

In the stent to be placed in bile duct according to the present invention, it is preferred that the sludge-resistant resin layer has a contact angle to water of 32° or less at a temperature of 22° C. In accordance with this embodiment, friction resistance of the bile circulating through the stent lumen on the stent inner peripheral surface can be made small; and hence, deposition of denatured materials of biological components, such as proteins or bile acid contained in bile, etc., on the stent inner peripheral surface, can be more effectively prevented, and an excellent effect for preventing deposition of sludge is revealed. Furthermore, flow resistance of the bile circulating through the stent lumen can be made small, and circularity of the bile is favorable.

In the stent to be placed in bile duct according to the present invention, it is preferred that concavities and convexities are formed on the outer peripheral surface of the stent. In accordance with this embodiment, the concavities and convexities formed on the outer peripheral surface of the stent come into close contact with the inner wall of the bile duct to obtain an anchoring effect, and hence, the movement of the stent can be suppressed, and the stent can be placed in a predetermined position over a long period of time.

In addition, the method for producing a stent to be placed in bile duct according to the present invention includes coating a coating liquid containing 0.1 to 0.5 mass % of a polymer obtained through polymerization of 2-methoxyethyl acrylate on the inner peripheral surface of a stent including a stent body of a cylindrical metal mesh tube and a cover member covering the outer periphery and/or inner periphery of the stent body, or on the inner peripheral surface of a stent of a cylindrical resin tube, thereby covering the inner peripheral surface of the stent by a sludge-resistant resin layer containing the polymer.

In accordance with the method for producing a stent to be placed in bile duct according to the present invention, by coating the coating liquid containing 0.1 to 0.5 mass % of a polymer obtained through polymerization of 2-methoxyethyl acrylate on the inner peripheral surface of the stent, the inner peripheral surface of the stent can be covered by a sludge-resistant resin layer on which denatured materials by biological components, such as proteins or bile acid contained in bile, etc., hardly deposit.

In the method for producing a stent to be placed in bile duct according to the present invention, it is preferred that the coating liquid is continuously or intermittently dropped on the inner peripheral surface of the stent while rotating the stent around a central axis of the stent as an axis of rotation, thereby coating the coating liquid on the inner peripheral surface of the stent. In accordance with this embodiment, the sludge-resistant resin layer can be formed in a substantially uniform film thickness on the inner peripheral surface of the stent, so that the deposition of sludge can be more effectively suppressed.

In the method for producing a stent to be placed in bile duct according to the present invention, it is preferred that the polymer obtained through polymerization of 2-methoxyethyl acrylate is subjected to a purification treatment by dipping in water or stirring for 6 hours or more. In accordance with this embodiment, unreacted monomers, polymers with a low degree of polymerization, and the like are removed by the purification treatment, and hence, a sludge-resistant resin layer on which sludge more hardly deposits can be formed.

Advantageous Effects of Invention

In accordance with the present invention, in view of the fact that the inner peripheral surface of the stent is covered by the sludge-resistant resin layer containing a polymer obtained through polymerization of 2-methoxyethyl acrylate, it is possible to suppress denaturation of biological components, such as proteins or bile acid contained in bile, etc., thereby preventing deposition of these denatured materials and the like on the stent inner peripheral surface. For this reason, even when the stent is placed in a bile duct over a long period of time, the stent lumen is hardly occluded by sludge, such as biliary sludge, etc., whereby functions as the stent can be ensured over a long period of time, and the frequency of replacement of the stent by removal and interchange, or the like can be reduced.

BRIEF DESCRIPTION OF DRAWINGS

FIGS. 5A and 5B show a stent body of the stent.

DESCRIPTION OF EMBODIMENTS

A first embodiment of the stent to be placed in bile duct according to the present invention is hereunder explained by reference to the accompanying drawings.

Figure 1:
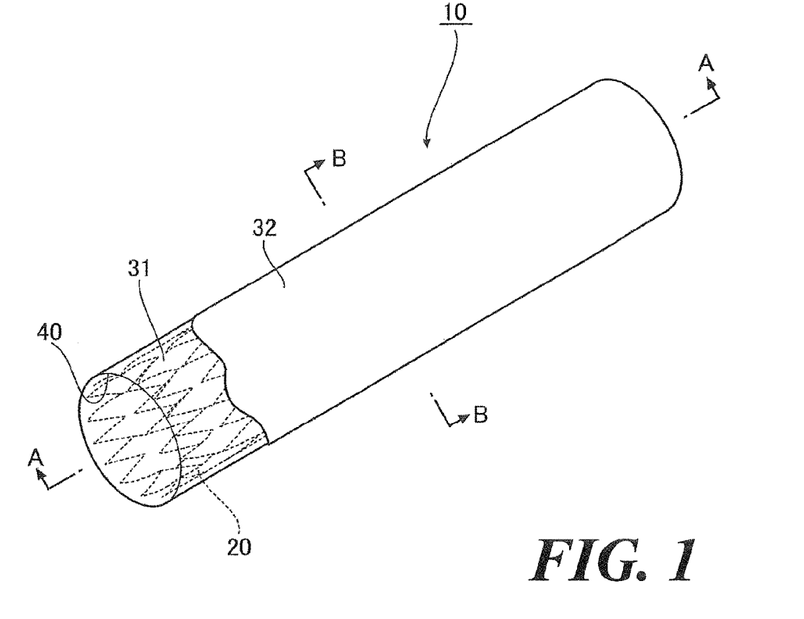
FIG. 1 is a diagrammatic view of a first embodiment of a stent to be placed in bile duct according to the present invention and is a perspective view in a cutaway state thereof.
Figure 2:
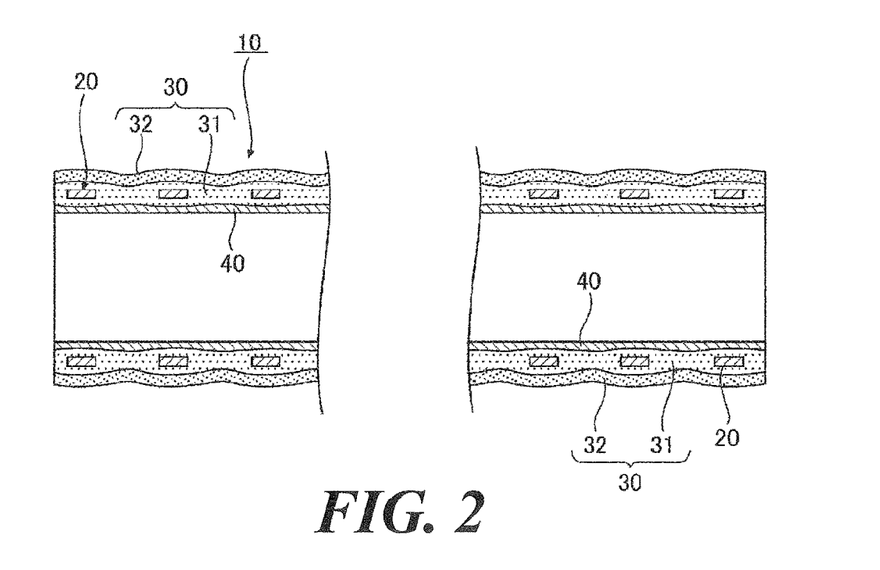
FIG. 2 is an A-A cross-sectional view of the stent.
Figure 3:
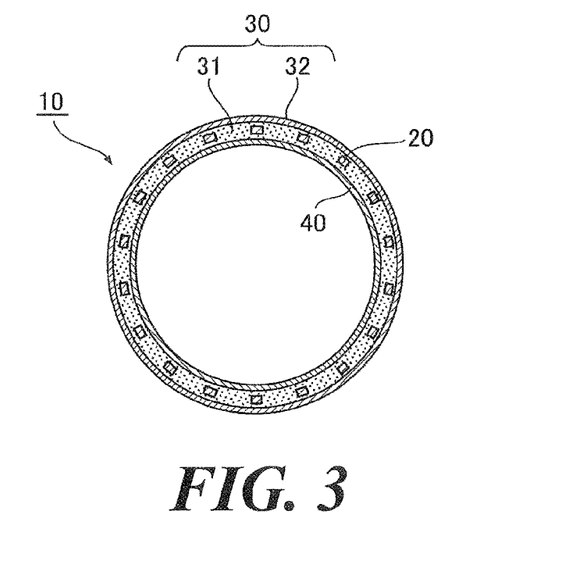
FIG. 3 is a B-B cross-sectional view of the stent.

As shown in FIGS. 1 to 3, a stent 10 to be placed in bile duct of this embodiment (hereinafter also referred to "stent") includes a stent body 20 of a cylindrical metal mesh tube, a cover member 30 covering the outer periphery and/or inner periphery of the stent body 20, and a sludge-resistant resin layer 40 covering the inner peripheral surface of the stent. In the stent according to the present invention, the sludge-resistant resin layer 40 is constituted of a resin layer containing a polymer obtained through polymerization of 2-methoxyethyl acrylate. The stent 10 is hereunder explained in detail.

Figure 4:
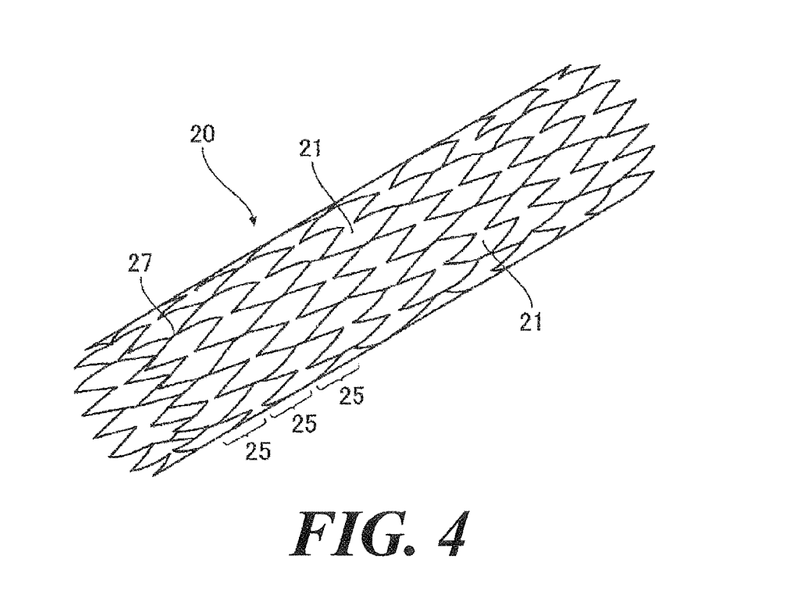
FIG. 4 is a diagrammatic view of a stent body of the stent.

First of all, the stent body 20 is explained while also referring to FIG. 4. This stent body 20 is a member formed by processing a metal cylinder or a metal sheet, or knitting metal wires and is formed in a cylindrical shape having mesh-shaped openings 21.

Figure 5A:
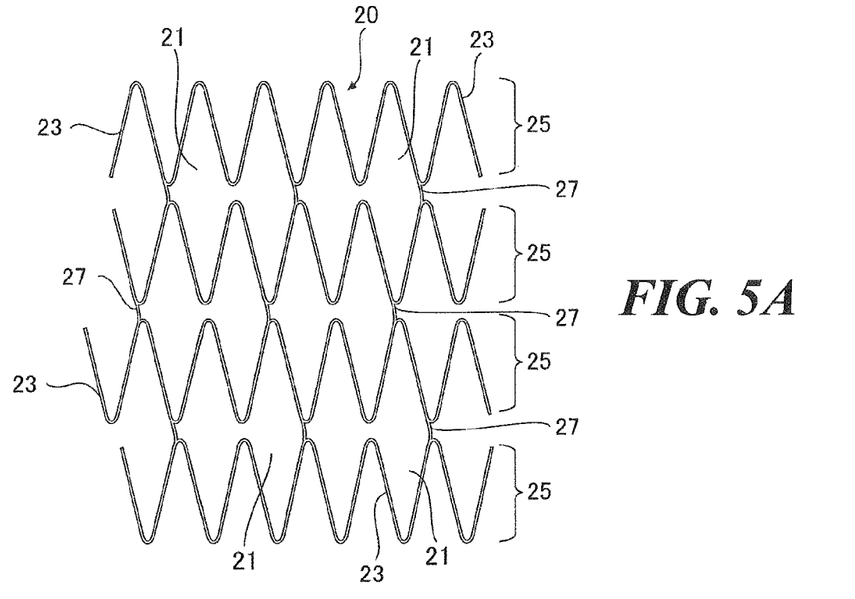
FIG. 5A is a development view.

Explanation is made while also referring to FIG. 5A. In this embodiment, a metal cylinder is subjected to laser processing, etching, or the like, thereby molding the stent body 20 in a cylindrical shape having mesh-shaped openings. That is, circumferential units 25 each extending in a zigzag shape along the circumferential direction, in which both ends of this zigzag-shaped portion 23 are annularly connected to each other, are formed. Bent portions of the zigzag-shaped portion 23 of each of the circumferential units 25 are connected to each other through a connection portion 27. According to this, the plural circumferential units 25 are connected to each other in the axial direction through the connection portions 27, whereby the stent body 20 is formed in a cylindrical shape as a whole.

Figure 5B:
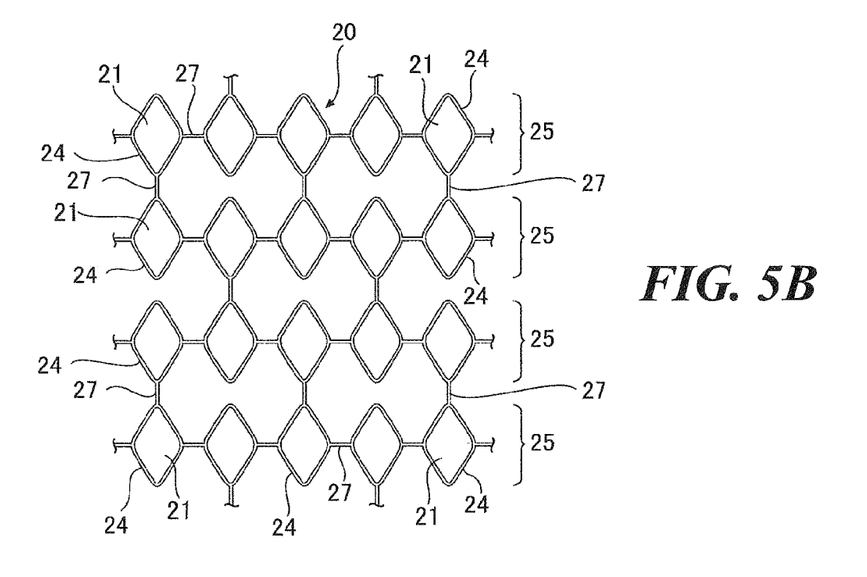
FIG. 5B is a development view of a stent body in other example.

The stent body 20 is not limited to the above-described form. The stent body 20 has only to have a cylindrical outer circumferential shape having the mesh-shaped openings 21. For example, as shown in FIG. 5B, the stent body 20 may be one in which plural frame-shaped bodies 24 each having the opening 21 are connected to each other in the circumferential direction to form the circumferential units 25, and these are connected to each other in the axial direction through the plural connection portions 27, thereby forming a cylinder shape. The disposition pattern of the mesh-shaped openings 21 of the stent body 20 is not limited to those described in the foregoing FIGS. 5A and 5B, and the disposition pattern is not particularly limited so long as it is diametrically contractable and expandable.

The stent body 20 may be formed by processing a metal sheet to form the plural circumferential units 25 having the zigzag-shaped portions 23 or frame-shaped bodies 24 and bending the resulting metal sheet in a cylindrical shape, or formed in a cylindrical shape by knitting metal wires by weaving, braiding, or entwining.

The stent body 20 may also be of a balloon-expandable type such that while it is a self-expandable type stent that is ordinarily in a diametrically-expanded state, by disposing a balloon in the inside of the stent and expanding it, the stent is diametrically expanded.

A material of the stent body 20 is not particularly limited. For example, stainless steel, Ta, Ti, Pt, Au, W, and the like and also shape memory alloys, such as an Ni—Ti-based alloy, a Co—Cr-based alloy, a Co—Cr—Ni-based alloy, a Cu—Zn—X (X=Al, Fe, etc.) alloy, an Ni—Ti—X (X=Fe, Cu, V, Co., etc.) alloy, etc., and the like are preferred.

Next, the cover member 30 is explained while also referring to FIGS. 2 and 3. In this embodiment, the cover member 30 is constituted of a polyurethane film 31 and a silicone film 32.

The polyurethane film 31 covers the stent body 20 so as to clog the mesh-shaped openings 21 of the stent body 20. In this embodiment, the stent body 20 is embedded in the polyurethane film 31.

As a material constituting the polyurethane film 31, for example, a polyether-based polyurethane, a polyester-based polyurethane, a polycarbonate-based polyurethane, a polycaprolactone-based polyurethane, and the like can be preferably used.

Although a film thickness of the polyurethane film 31 is not particularly limited, it is preferably 10 to 60 μm, and more preferably 20 to 40 μm. When the film thickness of the polyurethane film 31 is less than 10 μm, in the case of forming the silicone film 32 on the outer periphery of the polyurethane film 31, film formability of the silicone film 32 may be lowered. When the film thickness of the polyurethane film 31 exceeds 60 μm, there is a tendency that the whole diametrical size of the stent body 10 increases.

The silicone film 32 is formed so as to cover the outer periphery of the stent body 20 and the polyurethane film 31. In this embodiment, the stent body 20 is embedded in the polyurethane film 31, and hence, the silicone film 32 is covered on the outer periphery of the polyurethane film 31.

As a material constituting the silicone film 32, for example, a silicone resin, a silicone rubber, a silicone elastomer, and the like can be preferably used.

A film thickness of the silicone film 32 is preferably 5 to 60 μm, and more preferably 10 to 40 μm. When the film thickness of the silicone film 32 is less than 5 μm, an effect for suppressing hydrolysis of the polyurethane film 31 becomes hard to be obtained. When the film thickness of the silicone film 32 exceeds 60 μm, the whole diametrical size of the stent body 10 increases.

A total film thickness of the polyurethane film 31 and the silicone film 32, namely a film thickness of the cover membrane 30, is preferably 15 to 120 μm, and more preferably 20 to 100 μm.

In this embodiment, though the cover member 30 is constituted of a stack of the polyurethane film 31 and the silicone film 32, the cover member 30 may be a single layer of the polyurethane film 31. In the cover member 30, a resin, such as a silicone resin, a polyurethane resin, a nylon resin, a nylon elastomer, an olefin-based elastomer, e.g., polybutadiene, etc., a styrene-based elastomer, etc., or an interposed layer prepared by winding a flat film formed of such a resin, may be inserted between the polyurethane film 31 and the silicone film 32.

Next, the sludge-resistant resin layer 40 covering the stent inner peripheral surface is explained.

In the present invention, the sludge-resistant resin layer 40 is constituted of a resin layer containing a polymer obtained through polymerization of 2-methoxyethyl acrylate.

In this embodiment, the sludge-resistant resin layer 40 is formed on the inner peripheral side of the polyurethane film 31 of the cover member 30, and the stent inner peripheral surface is covered by the sludge-resistant resin layer 40.

The resin layer containing a polymer obtained through polymerization of 2-methoxyethyl acrylate is weak in an interaction with biological components, such as proteins or bile acid contained in bile, etc., and is able to suppress denaturation of these biological components and also to suppress deposition of denatured materials of these biological components, and the like. For this reason, by covering the inner peripheral surface of the stent by the above-described polymer-containing resin layer, occlusion of the stent lumen by sludge, such as biliary sludge, etc., can be prevented, and the functions as the stent can be maintained over a long period of time.

It may be considered that a reason for this resides in the following matter. That is, the polymer obtained through polymerization of 2-methoxyethyl acrylate, such as PMEA, etc., has water that is strong in an interaction with the polymer and does not freeze even at 0° C. or lower (bound water) and water that is low in an interaction with the polymer and freezes at around 0° C. (free water), and besides, water that is middle in an interaction with the polymer and does not freeze event at 0° C. or lower, but is provided with such properties that after supercooling to about −100° C., in a temperature rise process of gradually raising the temperature, freezes at around −40° C. (hereinafter referred to as "intermediate water"). In the bile, the biological components, such as proteins, biliary acid, etc., exist while taking a stable hydration structure. However, it may be considered that the hydration structure of the biological components, such as proteins or bile acid contained in bile, etc., is hardly broken due to the presence of the intermediate water, and as a result, denatured materials of these biological components, and the like hardly deposit.

Whether or not the polymer has the intermediate water can be confirmed by examining the structure of water in the polymer in an equilibrium hydration state by using a differential scanning calorimeter (DSC).

In the present invention, the polymer constituting the sludge-resistant resin layer 40 may be poly(2-methoxyethyl acrylate) (hereinafter referred to as "PMEA") obtained through homopolymerization of 2-methoxyethyl acrylate, or may also be a polymer obtained through copolymerization of 2-methoxyethyl acrylate with a monomer other than 2-methoxyethyl acrylate (hereinafter referred to as "other monomer"). Examples of the other monomer include alkoxyalkyl acrylates, such as 2-methoxymethyl acrylate, 2-methoxypropyl acrylate, 2-methoxybutyl acrylate, 2-ethoxymethyl acrylate, 2-ethoxyethyl acrylate, 2-ethoxypropyl acrylate, 2-ethoxybutyl acrylate, etc.; alkoxyalkyl methacrylates, such as 2-methoxyethyl methacrylate, 2-methoxymethyl methacrylate, 2-methoxypropyl methacrylate, 2-methoxybutyl methacrylate, 2-ethoxymethyl methacrylate, 2-ethoxyethyl methacrylate, 2-ethoxypropyl methacrylate, 2-ethoxybutyl methacrylate, etc.; and the like.

The above-described polymer is especially preferably PMEA. PMEA contains a large quantity of intermediate water, and a more excellent effect for preventing deposition of sludge is obtained. A number average molecular weight of PMEA is preferably 10,000 to 500,000, and more preferably 30,000 to 100,000. When the number average molecular weight of PMEA is less than 10,000, the deposition of sludge may not be sufficiently prevented. When the number average molecular weight of PMEA exceeds 500,000, PMEA is liable to be coagulated, and on the occasion of forming a film, fine concaves and convexes are liable to be produced on the surface, and hence, there is a tendency that a coating film with excellent surface smoothness becomes difficult to be formed.

A moisture content of the above-described polymer is preferably 7 to 15 mass %, and more preferably 8 to 10 mass %. So long as the moisture content of the polymer falls within the foregoing range, the effect for preventing deposition of sludge can be made more favorable. The moisture content of the polymer can be determined according to the following formula.

Moisture content=((Mass of water in polymer)/(Mass of water-containing polymer))×100

Here, the mass of the water-containing polymer is a total value of a mass of the dry polymer and a mass of water.

A film thickness of the sludge-resistant resin layer 40 is preferably 0.1 to 10 μm, and more preferably 1 to 10 μm. When the film thickness of the sludge-resistant resin layer 40 exceeds 10 μm, the polymer is coagulated at the time of film formation, whereby concaves and convexes are liable to be produced on the surface. When the film thickness of the sludge-resistant resin layer 40 is less than 0.1 μm, there is a tendency that the durability is lowered.

A contact angle to water of the sludge-resistant resin layer 40 at a temperature of 22° C. is preferably 32° or less, and more preferably 30° or less. So long as the contact angle to water of the sludge-resistant layer 40 is 32° or less, friction resistance of the bile circulating through the stent lumen on the stent inner peripheral surface can be made small; and hence, deposition of denatured materials of biological components, such as proteins or bile acid contained in bile, etc., on the stent inner peripheral surface can be more effectively prevented, and an excellent effect for preventing deposition of sludge is revealed. Furthermore, flow resistance of the bile circulating through the stent lumen can be made small, and circularity of the bile can be made favorable. In the present invention, the contact angle is a value as measured by means of the static contact angle measurement method at 22° C.

Next, the method for producing a stent to be placed in bile duct according to the present invention is explained while taking as an example a method for producing the stent to be placed in bile duct of the foregoing embodiment as shown in FIGS. 1 to 3.

First of all, the stent body 20 is covered by the polyurethane film 31. A method for forming the polyurethane film 31 is not particularly limited, and it can be achieved by conventionally known methods. Examples thereof include forming methods, such as a dipping method, a casting method, a coating method, an extrusion molding method, a spray atomizing method, etc. The polyurethane film 31 can also be formed by inserting a polyurethane tube into the inner periphery of the stent body 20 and cladding this onto the stent body 20. The stent body 20 may also be covered by the polyurethane film 31 by covering a polyurethane tube on the outer periphery of the stent body 20, followed by contraction in diameter by means of solvent drying, heat shrinkage, or the like. In the case of embedding the stent body 20 in the polyurethane film 31 as in this embodiment, it is preferred to form the polyurethane film 31 by adopting a dipping method or a coating method.

Next, the outer periphery of the polyurethane film 31 is covered by the silicone film 32. A method for forming the silicone film 32 is not particularly limited, and it can be achieved by conventionally known methods. Examples thereof include forming methods, such as a dipping method, a casting method, a coating method, an extrusion molding method, a spray atomizing method, etc. The outer periphery of the polyurethane film 31 may be covered by the silicone film 32 by covering a silicone tube on the outer periphery of the polyurethane film 31, followed by contraction in diameter by means of solvent drying, heat shrinkage, or the like.

Subsequently, a coating liquid containing a polymer obtained through polymerization of 2-methoxyethyl acrylate is coated on the inner peripheral surface of the polyurethane film 31 as the inner peripheral surface of the stent and then dried, thereby covering the inner peripheral surface of the stent by the sludge-resistant resin layer 40 constituted of the above-described polymer-containing resin layer. In this way, the stent as shown FIGS. 1 to 3 can be produced.

A preferred example of the method for coating the coating liquid as described above is explained by referring to FIG. 6.

Figure 6:
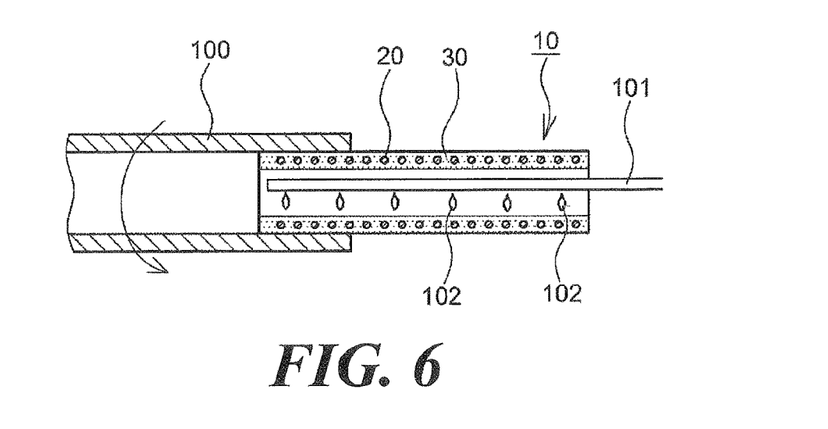
FIG. 6 is an explanatory view showing a production method of the stent.

First of all, one end of the stent 10 is inserted into a cylindrical jig 100, thereby supporting the stent 10 by the jig 100. A material of the jig 100 is not particularly limited. Examples thereof include polytetrafluoroethylene and the like. Then, the jig 100 is rotated in an arrow direction in the figure by a non-illustrated driving device. According to this, the stent 10 supported by the jig 100 is rotated around a central axis of the stent 10 as an axis of rotation. Then, a nozzle 101 provided with one or plural discharge ports is inserted into the stent inner periphery, and a coating liquid 102 is continuously or intermittently dropped in this state on the inner peripheral surface of the stent from each of the discharge ports. According to this, the coating liquid can be coated in a substantially uniform film thickness on the stent inner peripheral surface by the action of a centrifugal force.

The timing of rotating the stent 10 may be simultaneous with the timing of dropping the coating liquid. The stent 10 may be rotated after dropping the coating liquid. A rotation rate of the stent 10 is not particularly limited. The rotation rate of the stent 10 varies depending upon an inner diameter of the stent or the like. It is preferred to properly select conditions under which the coating liquid can be coated in a uniform film thickness on the stent inner periphery. In FIG. 6, though one end of the stent 10 is held by the jig 100, the entire outer periphery of the stent 10 may be held by the jig 100, too.

In the present invention, it is preferred to use the polymer obtained through polymerization of 2-methoxyethyl acrylate after performing a purification treatment by dipping in water or stirring for 6 hours or more. The polymer after the polymerization contains unreacted monomers, polymers with a low degree of polymerization, and the like. However, the unreacted monomers, the polymers with a low degree of polymerization, and the like are removed by performing a purification treatment, and hence, a sludge-resistant resin layer on which sludge more hardly deposits can be formed.

In the present invention, as for the coating liquid, it is preferred to use one containing the above-described polymer in a content of 0.1 to 0.5 mass %, and the content of the polymer in the coating liquid is more preferably 0.2 to 0.5 mass %, and especially preferably 0.2 to 0.4 mass %. When the content of the above-described polymer is less than 0.1 mass %, deposition of sludge may not be sufficiently prevented. When the content of the above-described polymer exceeds 0.5 mass %, the polymer is liable to be coagulated, and there is a tendency that fine concaves and convexes are liable to be produced on the film surface, thereby depositing sludge.

A solvent contained in the coating liquid is not particularly limited, and conventionally known solvents can be used. Examples thereof include alcohols, such as methanol, ethanol, propanol, etc., chloroform, acetone, toluene, xylene, hexane, and the like.

In the present invention, a drying condition of the coating liquid coated on the inner peripheral surface of the stent is not particularly limited. The drying may be normal temperature drying, or it may also be heat drying. In the case of heat drying, a drying temperature is preferably lower than 100° C., and more preferably lower than 80° C. When the drying temperature exceeds 100° C., the polymer may be coagulated at the time of drying, whereby concaves and convexes are produced on the film surface.

Figure 7:
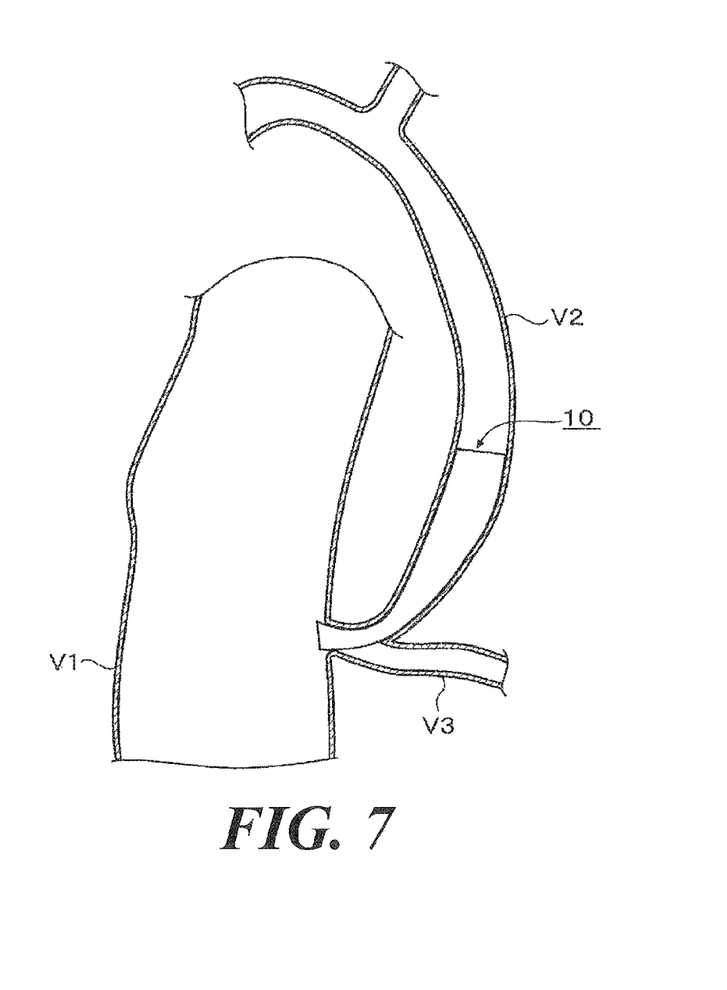
FIG. 7 is an explanatory view showing a state of use of the stent.

Next, an example of a method for using the stent 10 having the above-described structure is explained by reference to FIG. 7.

First of all, the stent 10 is diametrically contracted and received in the inner periphery of a distal end portion of a non-illustrated medical tube, such as a sheath, a catheter, etc. Then, according to a well-known method, a non-illustrated endoscope is operated to pass through an oral cavity, a stomach, or the like and move to a duodenum V1 (see FIG. 7), and a non-illustrated guide wire is introduced into a bile duct V2 through the lumen of the endoscope, so that a distal end portion of the guide wire reaches a position slightly beyond a stenosed affected site of the bile duct V2.

Thereafter, the medical tube having the stent 10 received therein is conveyed through the guide wire, thereby bringing the distal end portion of the medical tube to the affected site of the bile duct V2. A pusher or the like is inserted into the medical tube in that state, and the stent 10 is pushed out from the distal end of the medical tube through this pusher or the like, whereby the stent 10 is diametrically expanded as shown in FIG. 7, and the stent 10 is placed in the bile duct V2.

In this stent 10, the inner peripheral surface of the stent is covered by the sludge-resistant resin layer 40 containing a polymer obtained through polymerization of 2-methoxyethyl acrylate, and hence, denaturation of biological components, such as proteins or bile acid contained in bile, etc., can be suppressed, and deposition of these denatured materials and the like on the stent inner peripheral surface can be prevented. For this reason, even when the stent 10 is placed in the bile duct over a long period of time, the stent lumen is hardly occluded by sludge, such as biliary sludge, etc., whereby functions as the stent can be ensured over a long period of time, and the frequency of replacement of the stent can be reduced.

In the stent 10 of this embodiment, the outer periphery of the polyurethane film 31 is covered by the silicone film 32 having a good affinity with the polyurethane, and hence, the silicone film in which pinholes are apt to be produced can be made thin and formed uniformly, so that it becomes possible to downsize the stent 10. In consequence, the stent 10 can be received even in a catheter having a small inner diameter, and hence, even in the case of placing the stent 10 so as to bypass between the stomach and the bile duct or between the duodenum and the bile duct through an ultrasonic endoscope, it becomes possible to decrease the number of times of use of a tube, a dilator, or the like for enlarging a puncture hole toward each organ or tissue or the like, and leakage of the bile from the bile duct V2 or the like is prevented as far as possible, thereby enabling invasion into the body to be suppressed.

Hydrolysis of the polyurethane film 31 can be prevented by the silicone film 32 that is hardly hydrolyzed, and hence, it is possible to place the stent 10 over a long period of time.

Figure 8:
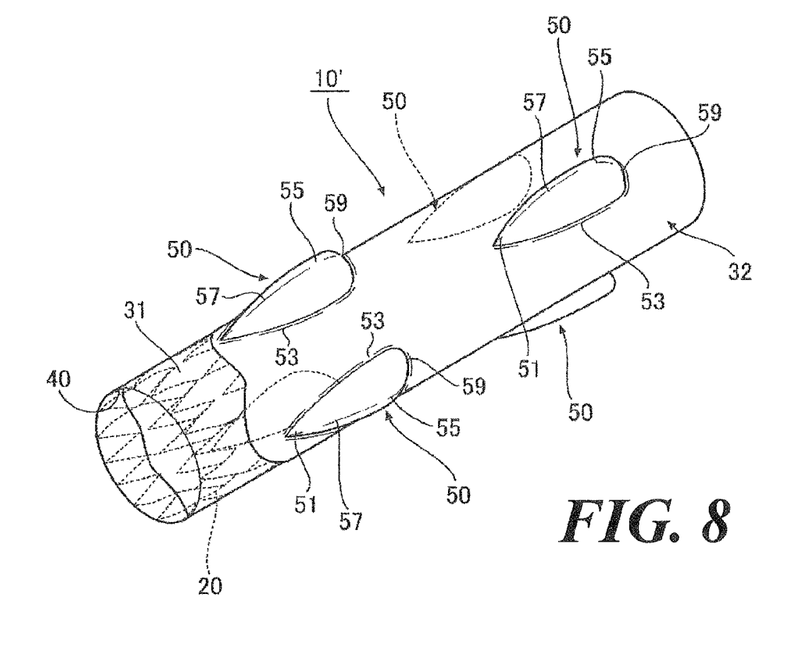
FIG. 8 is a diagrammatic view of a second embodiment of a stent to be placed in bile duct according to the present invention and is a perspective view in a cutaway state thereof.

Next, a second embodiment of the stent to be placed in bile duct according to the present invention is hereunder explained by reference to FIG. 8.

The second embodiment is different from the foregoing first embodiment at a point where this stent 10' is provided with protrusions 50 on the outer peripheral surface thereof.

A shape of the protrusion 50 is not particularly limited. The protrusion 50 preferably has a shape which extends with a predetermined width in the circumferential direction and with a predetermined length in the axial direction and is formed into a shape protruding smoothly so as to bulge gradually and then decline gradually.

The protrusion 50 in this embodiment has a tapered shape with sharpness on the side of a distal end 51 in the axial direction and has an approximately water-drop-like shape which is diametrically expanded such that a width between opposite edges 53 and 53 increases gradually toward the axially proximal end side while the edges 53 and 53 draw curves.

The outer periphery of the protrusion 50 along the axial direction of the stent 10' has a shape which bulges gradually higher in level from the side of the distal end 51 toward a vertex portion 55 (a portion protruding highest in level with respect to the outer periphery of the stent 10') and then declines gradually from this vertex portion 55 toward the proximal end side.

The outer periphery of the protrusion 50 along the circumferential direction of the stent 10' also has a shape which bulges gradually higher in level from one end in the circumferential direction toward the vertex portion 55 and then declines gradually from the vertex portion 55 toward the other end in the circumferential direction. For that reason, the protrusion 50 has a shape bulging smoothly as a whole without any corner portion, any edge portion, or the like on the circumferential surface thereof.

Inclination of the protrusion 50 along the axial direction of the stent 10' is formed such that a slope corresponding to the direction of taking out the stent 10' with respect to the vertex portion 55, namely a slope 57 on the distal end side extending from the distal end 51 in the axial direction to the vertex portion 55 is gentler than an opposite slope to the slope 57, namely a slope 59 on the proximal end side extending from the vertex portion 55 to the proximal end in the axial direction.

In accordance with the stent of this embodiment, on the occasion of placing the stent 10' in the bile duct, the protrusions 50 formed on the outer periphery of the stent 10' bite into an inner wall of the bile duct and come into close contact therewith. For this reason, the movement of the stent 10' within the bile duct can be effectively prevented due to an anchoring effect, and the stent 10' can be stably placed at a predetermined position within the bile duct over a long period of time.

Figure 9:
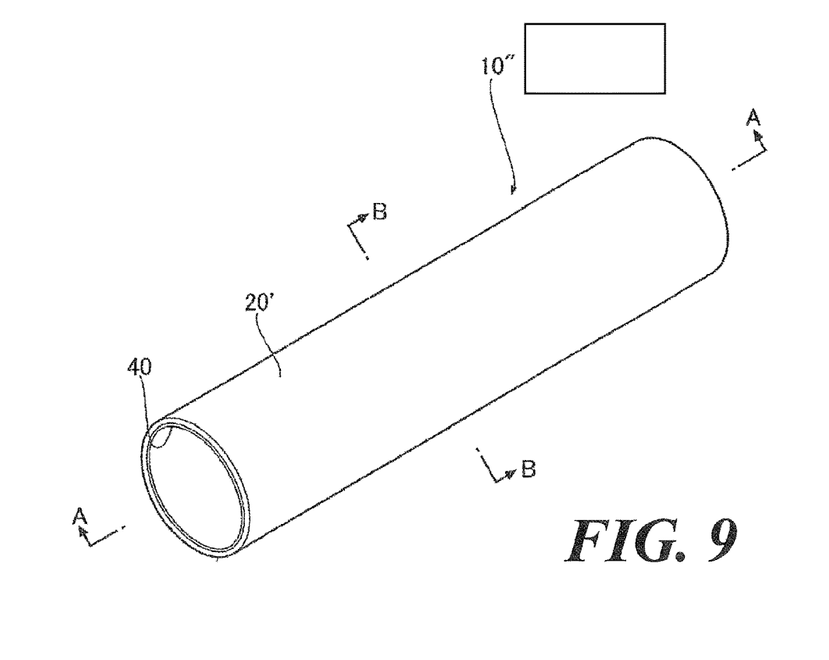
FIG. 9 is a diagrammatic view of a third embodiment of a stent to be placed in bile duct according to the present invention.
Figure 10:
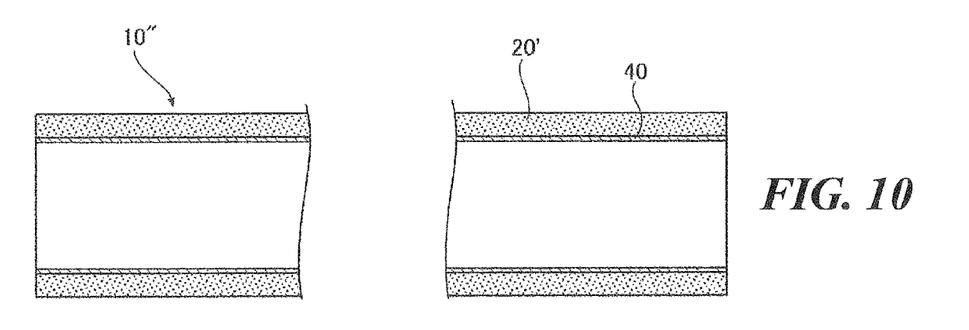
FIG. 10 is an A-A cross-sectional view of the stent.
Figure 11:
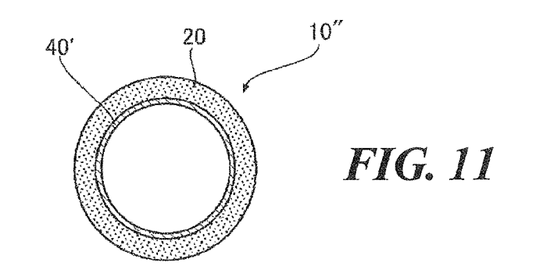
FIG. 11 is a B-B cross-sectional view of the stent.

Next, a third embodiment of the stent to be placed in bile duct according to the present invention is hereunder explained by reference to FIGS. 9 to 11.

This stent 10" includes a stent body 20' of a cylindrical resin tube and a sludge-resistant resin layer 40 covering the inner peripheral surface of the stent.

A material of the stent body 20' is not particularly limited. A resin having flexibility, such as a polyurethane resin, etc., is preferably used.

EXAMPLES

In the following Examples, a polymer prepared by subjecting PMEA having a molecular weight of 85,000, which had been obtained through radical polymerization of 2-methoxyethyl acrylate in the presence of azobisisobutyronitrile, to a purification treatment by dipping in pure water and stirring for 6 hours, is used as the "polymer obtained through polymerization of 2-methoxyethyl acrylate". The term "PMEA" as referred to hereunder means PMEA which had been subjected to the above-described purification treatment.

Test Example 1

Each of coating liquids is coated on a glass plate by the spin coating method, thereby forming a 0.5 μm-thick film. As the coating liquids, those prepared by dissolving 0.2 mass % of PMEA, polystyrene (PS), polyethylene terephthalate (PET), polyurethane, and silicone, respectively in methanol are used.

The glass plates having the coating liquid of every sort coated thereon and a glass plate not coated with a coating liquid are set in a 16-well container (made of polyethylene). Then, 0.5 mL of a bile solution (a solution prepared by dissolving 0.02 mg/mL of a bovine bile powder (manufactured by Wako Pure Chemical Industries, Ltd.) in a phosphate buffer solution (PBS solution)) is poured onto each of the glass plates and allowed to stand at 37° C. or 50° C. for 6 days.

Thereafter, the bile solution within each of the wells is sucked and removed, and the inside of the well is washed three times with 500 μL of a phosphate buffer solution (PBS solution) and then washed once with 1,000 μL of pure water. Then, pure water is poured into the well, and any deposit is observed by an optical microscope. The test results at 37° C. are shown in FIG. 12, and the test results at 50° C. are shown in FIG. 13.

Figure 12:
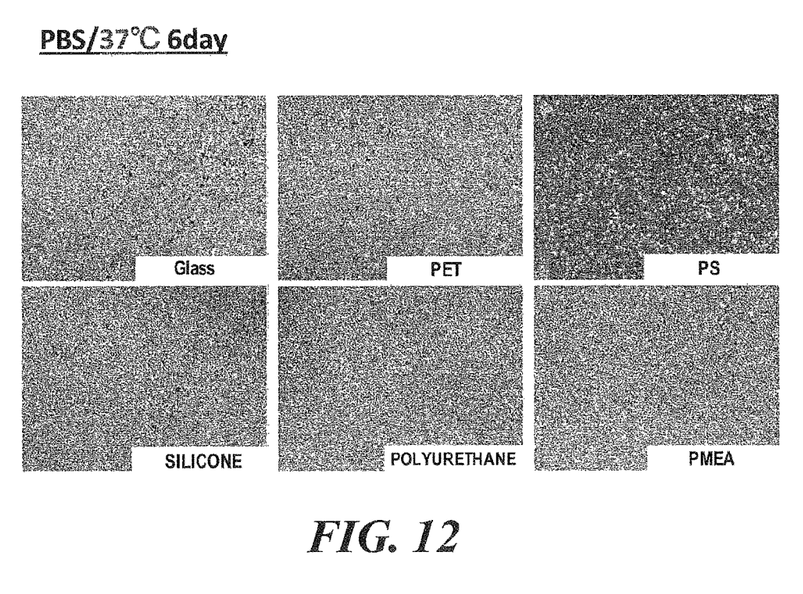
FIG. 12 is a view showing the test results of Test Example 1 at 37° C.
Figure 13:
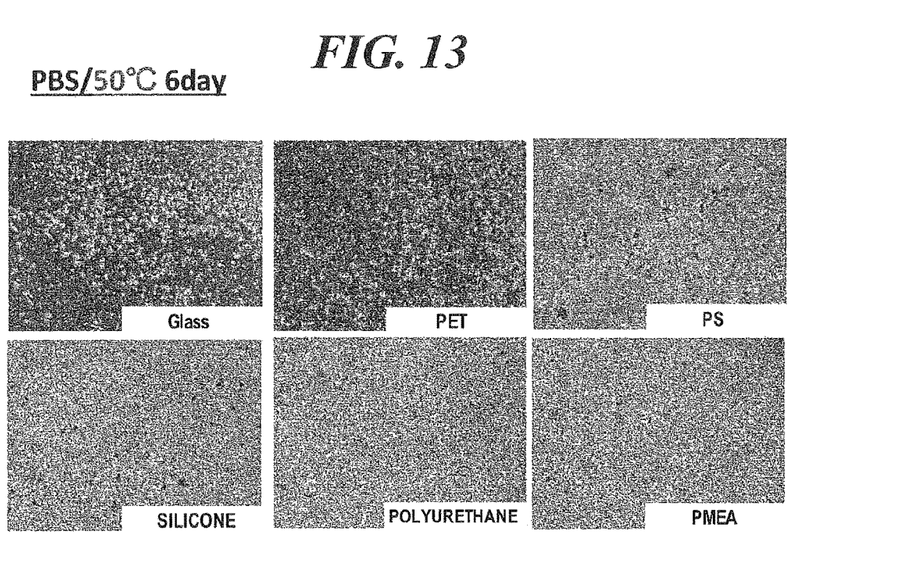
FIG. 13 is a view showing the test results of Test Example 1 at 50° C.

From the results shown in FIGS. 12 and 13, with respect to PMEA, the sludge (black spots in the figure) is small, and the deposition amount of sludge is low. For this reason, it is noted that PMEA is excellent in resistance to sludge.

Test Example 2

Each of coating liquids is coated on a glass plate by the spin coating method, thereby forming a 0.5 μm-thick film.

As the coating liquids, those prepared by dissolving 0.2 to 1.5 mass % of PMEA in methanol are used.

The glass plates having the coating liquid of every sort coated thereon are set in a 16-well container (made of polyethylene). Then, 0.5 mL of a bile solution (a solution prepared by dissolving 0.02 mg/mL of a bovine bile powder (manufactured by Wako Pure Chemical Industries, Ltd.) in a phosphate buffer solution (PBS solution)) is poured onto each of the glass plates and allowed to stand at 37° C. for 7 days.

Thereafter, the bile solution within each of the wells is sucked and removed, and the inside of the well is washed three times with 500 μL of a phosphate buffer solution (PBS solution) and then washed once with 1,000 μL of pure water. Then, pure water is poured into the well, and any deposit is observed by an optical microscope. The test results are shown in FIG. 14.

Figure 14:
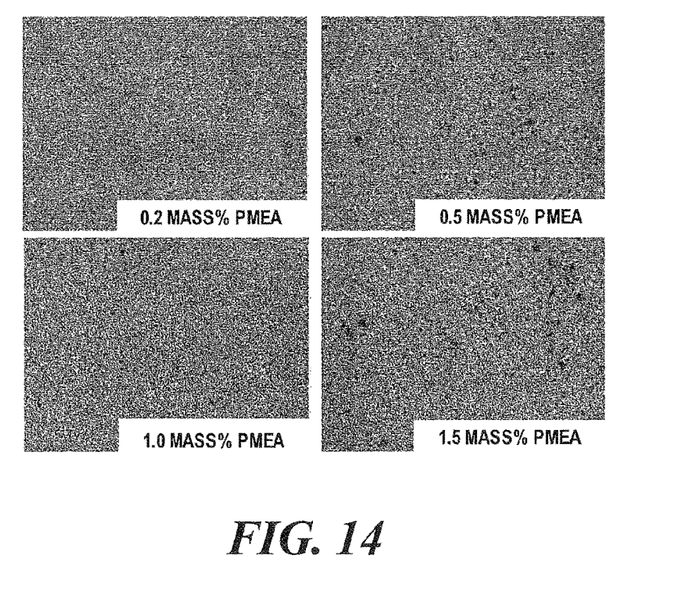
FIG. 14 is a view showing the test results of Test Example 2.

From the results shown in FIG. 14, in the case of using the coating liquid having a PMEA concentration of 0.2 mass %, the sludge is particularly hardly deposited, so that excellent resistance to sludge is revealed. It may be considered that a reason for this resides in the matter that in the case of using a coating liquid containing PMEA in a high concentration, PMEA is coagulated to produce unevenness of concaves and convexes on the surface, and sludge is accumulated thereon.

Test Example 3

The outer periphery of a stent body of a cylindrical metal mesh tube is covered by a polyurethane film such that mesh-shaped openings are clogged, and the outside of the resultant is further covered by a silicone film. Then, as shown in FIG. 6, one end of the stent is inserted into the cylindrical jig 100, and the jig 100 is rotated in an arrow direction in the figure. Then, a coating liquid prepared by adding PMEA to methanol (PMEA concentration: 0.2 mass %) is coated in a coating amount of 0.2 to 1.0 mL/cm² on the stent inner periphery, followed by drying at 40° C. for 6 hours.

After drying, a contact angle to water of the stent inner periphery at 22° C. is measured. The results are shown in Table 1.

TABLE 1

| Coating amount of coating liquid (mL/cm²) | Contact angle |
| --- | --- |
| 0 | 47.5° |
| 0.2 | 29.2° |
| 0.5 | 34.9° |
| 1 | 34.3° |

Test Example 4

A stent in which a cover member constituted of a silicone film is disposed on the outer periphery of a metal mesh tube (hereinafter referred to as "silicone film-based stent") (two kinds); a stent in which a cover member constituted of a polyurethane film is disposed on the outer periphery of a metal mesh tube (hereinafter referred to as "polyurethane film-based stent") (n=3); a stent in which a cover member constituted of a fluorine resin film is disposed on the outer periphery of a metal mesh tube (hereinafter referred to as "fluorine resin film-based stent") (n=1); a stent in which a cover member constituted of a polyurethane film is disposed on the outer periphery of a metal mesh tube, and a coating liquid of a PMEA/methanol solution (PMEA concentration: 0.2 mass %) is coated in the inside (stent inner peripheral surface) of the metal mesh tube having the cover member disposed thereon, thereby covering the stent inner periphery by PMEA (hereinafter referred to as "0.2 mass % PMEA-coated stent") (n=3); and a stent in which a cover member constituted of a polyurethane film is disposed on the outer periphery of a metal mesh tube, and a coating liquid of a PMEA/methanol solution (PMEA concentration: 0.5 mass %) is coated in the inside (stent inner peripheral surface) of the metal mesh tube having the cover member disposed thereon, thereby covering the stent inner periphery by PMEA (hereinafter referred to as "0.5 mass % PMEA-coated stent") (n=3) are used.

Figure 15:
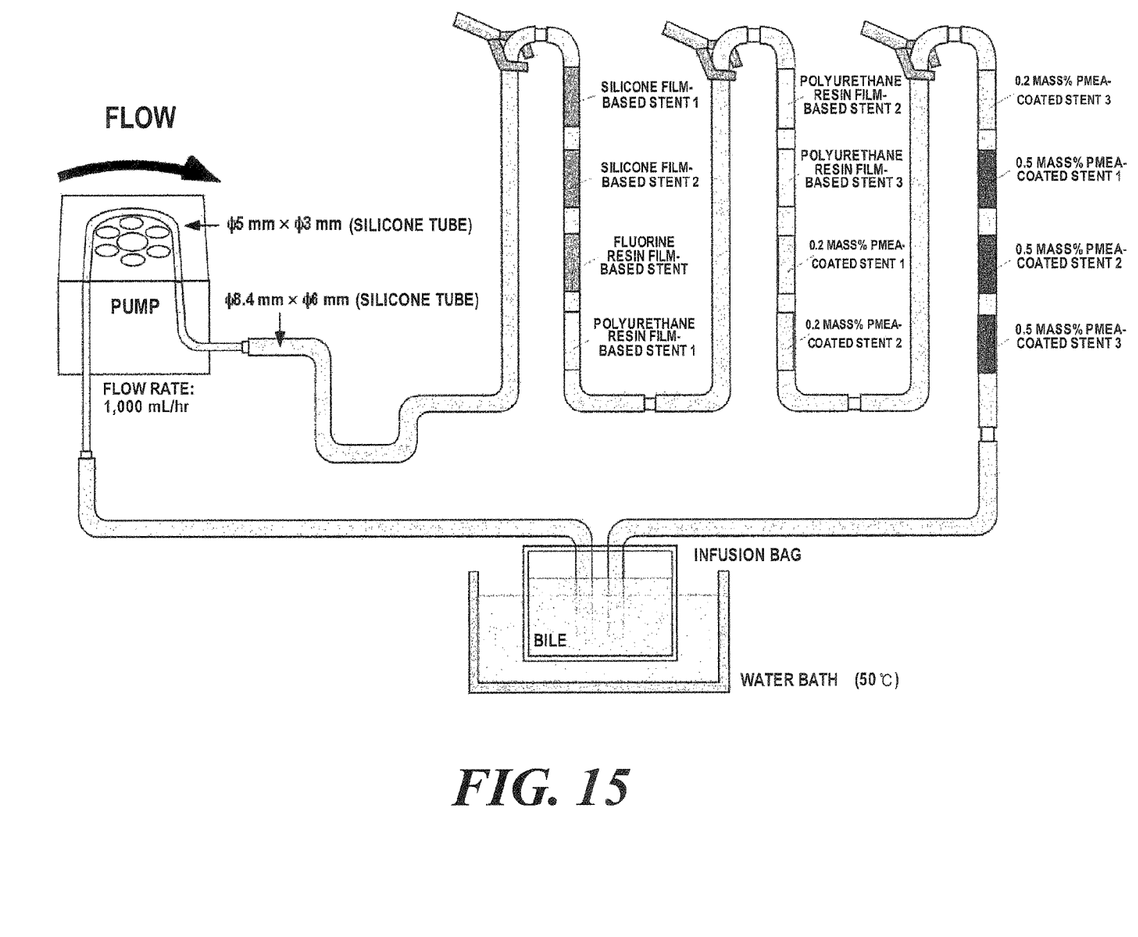
FIG. 15 is a diagrammatic view of a test apparatus used in Test Example 4.

Each of the above-described stents (8 mm in outer diameter×80 mm in length) is disposed on the inner tube side of a silicone tube (outer diameter: 8.4 mm, inner diameter: 6 mm) of a test apparatus shown in FIG. 15. Then, a peristaltic pump and an infusion bag are connected to each other, thereby forming a circuit. Then, a bile solution (a solution prepared by dissolving 0.02 g/mL of a bovine bile powder (manufactured by Wako Pure Chemical Industries, Ltd.) in a phosphate buffer solution (PBS solution)) is charged in the infusion bag, the peristaltic pump is actuated while heating the infusion bag at 50° C. in a water bath, and the bile solution is circulated at a flow rate of 1,000 mL/hr. After a lapse of 14 days, the presence or absence of sludge of each of the stents is observed through visual inspection.

With respect to the silicone film-based stent and the fluorine resin film-based stent, a large quantity of a white alga-like solid is produced on the inner tube side. In the polyurethane film-based stent, a white alga-like solid is slightly produced on the inner tube side.

On the other hand, with respect to the 0.2 mass % PMEA-coated stent and the 0.5 mass % PMEA-coated stent, a white alga-like solid is not substantially produced. In particular, with respect to the 0.2 mass % PMEA-coated stent, the amount of the white alga-like solid as produced is extremely low.

From these test results, it is noted that PMEA is very excellent in resistance to sludge even in the circulation system.

REFERENCE SIGN LIST 10, 10', 10": Stent
20, 20': Stent body
30: Cover member
40: Sludge-resistant resin layer

The invention claimed is:

1. A stent to be placed in a bile duct, the stent comprising:
a stent body of a cylindrical metal mesh tube; and
a cover member covering an outer periphery and/or an inner periphery of the stent body,
wherein an inner peripheral surface of the stent is covered by a sludge-resistant resin layer comprising a coating material of a polymer of 2-methoxyethyl acrylate,
wherein the cover member includes a polyurethane film embedding the stent body and a silicone film disposed on an outer periphery of the polyurethane film, and
wherein the sludge-resistant resin layer is disposed on an inner periphery of the polyurethane film of the cover member.

2. The stent to be placed in the bile duct of claim 1, wherein the sludge-resistant resin layer has a contact angle to water of 32° or less at a temperature of 22° C.

3. The stent to be placed in the bile duct of claim 1, wherein the sludge-resistant resin layer includes a resin layer formed by coating the coating material containing 0.1 mass % to 0.2 mass % of the polymer obtained through the polymerization of 2-methoxyethyl acrylate on the inner peripheral surface of the stent.

4. The stent to be placed in the bile duct of claim 1, wherein concavities and convexities are formed on an outer peripheral surface of the stent.

5. The stent to be placed in the bile duct of claim 1, wherein a thickness of the sludge-resistant resin layer is in a range from 0.1 µm to 10 µm.

6. The stent to be placed in the bile duet of claim 1, wherein a thickness of the sludge-resistant resin layer is in a range from 1 µm to 10 µm.

7. The stent to be placed in the bile duct of claim 1, wherein the cover member is disposed on the inner periphery of the stent body.

8. The stent to be placed in the bile duet of claim 1, wherein the polyurethane film is disposed on an upper surface of the sludge-resistant resin layer.

9. The stent to be placed in the bile duct of claim 1, wherein an average molecular weight of the polymer is in a range from 10,000 to 500,000.

10. The stent to be placed in the bile duct of claim 1, wherein an entirety of the inner peripheral surface of the stent is covered by the sludge-resistant resin layer.

11. A stent to be placed in a bile duct, the stent comprising:
a stent body of a cylindrical metal mesh tube; and
a cover member covering at least one of an outer periphery of the stent body and an inner periphery of the stent body,
wherein an inner peripheral surface of the stent is covered by a sludge-resistant resin layer formed by coating a coating material containing 0.1 mass % to 0.5 mass % of a polymer of 2-methoxyethyl acrylate,
wherein the cover member includes a polyurethane film embedding the stent body and a silicone disposed on an outer periphery of the polyurethane film,
wherein the sludge-resistant resin layer is disposed on an inner periphery of the polyurethane film of the cover member, and
wherein a thickness of the sludge-resistant resin layer is in a range from 0.1 µm to 10 µm.

12. The stent to be placed in the bile duet of claim 1, wherein, in a cross-sectional view of the stent, the polyurethane film is disposed on an outer surface of the stent body.

13. The stent to be placed in the bile duct of claim 1, wherein, in a cross-sectional view of the stent, the polyurethane film is disposed on an entirety of the stent body.

14. The stent to be placed in the bile duct of claim 1, wherein, in a cross-sectional view of the stent, an entirety of the stent body is spaced apart from the sludge-resistant resin layer and the silicone film.

* * * * *